United States Patent [19]

Geho

[11] Patent Number: 4,704,394
[45] Date of Patent: Nov. 3, 1987

[54] TREATMENT FOR HYPERACTIVITY

[75] Inventor: W. Blair Geho, Wooster, Ohio

[73] Assignee: Technology Unlimited, Inc., Wooster, Ohio

[21] Appl. No.: 887,258

[22] Filed: Jul. 21, 1986

Related U.S. Application Data

[63] Continuation-in-part of Ser. No. 604,154, Apr. 25, 1984, Pat. No. 4,602,043, which is a continuation-in-part of Ser. No. 514,492, Jul. 18, 1983, abandoned.

[51] Int. Cl.$^4$ .................. A61K 31/44; A61K 31/405; A61K 31/445
[52] U.S. Cl. .................................. 514/288; 514/315; 514/415
[58] Field of Search ................... 514/315, 415, 288

Primary Examiner—Stanley J. Friedman
Attorney, Agent, or Firm—Frijouf, Rust & Pyle

[57] ABSTRACT

This invention is for an improved method of treating hyperkinetic behavior based on the discovery of the etiology of the disorder. The genesis of the invention is in the discovery that constant overactivity, distractibility, impulsiveness, and aggressiveness, is frequently related to hypoglycemia. It has been discovered that hyperkinetic behavior due to moderate hypoglycemia will respond favorably, to the treatment of hypoglycemia. Hypoglycemia occurs during fasting and is due to an inappropriate presence of serotonin at the liver. Serotonin is a key hormone in conjunction with insulin to program liver glucose control. From this, the method is described of using a serotonin antagonist or an agent to block synthesis and/or storage of serotonin after glucose is no longer supplied to the portal vein. Then the liver can cease glucose uptake and begin production of glucose for the peripheral blood supply. The preferred serotonin antagonist is cyproheptadine.

Increased blood serotonin levels, in a fasting state, causes hepatic retention of glucose and a degree of hypoglycemia. The body corrects the hypoglycemia by activating the adrenergic nervous system. Adrenergic correction of hypoglycemia is followed by regression, then adrenergic correction again on and on in prolonged cycle. The adrenergic correction is associated with overactivity and behavioral (characteristics associated with the well known "fight and flight" response). Although the activity lessens as a child grows older, and often disappears by adolescence, some mental disorders are probably the result of prolonged mild hypoglycemia.

5 Claims, 2 Drawing Figures

TREATMENT FOR HYPERACTIVITY

RELATED SUBJECT MATTER

This application is a continuation-in-part of application Ser. No. 604,154, filed Apr. 25, 1984, now U.S. Pat. No. 4,602,043, which is in turn a continuation-in-part of Ser. No. 514,492, filed July 18, 1983, now abandoned.

BACKGROUND OF THE INVENTION

1. Field of the Invention

Therapeutic methods for control of hyperkinetic activity in warm blooded animals, including humans.

2. Information Disclosure Statement

Glucose in the blood is a primary energy nutrient for the body. Its level in the blood is carefully controlled so that it neither goes too high nor too low. Maintaining a constant blood level of glucose is so important that the body has, within the limits of current understanding of physiology, surprisingly sophisticated hormonal systems to prevent both hyperglycemia (blood glucose too high) and hypoglycemia (blood glucose too low).

The body has diseases that are characterized by blood glucose levels that are either too high (i.e., Diabetes Mellitus types I and II) or too low (i.e., hypoglycemia). This disclosure describes improved therapeutic means to correct abnormal swings in blood glucose levels and resultant hyperkinetic activity.

This invention recognizes the etiologies of these diseases of glucose metabolism. In order to understand the use of these new therapeutic inventions, it is necessary to describe the normal physiological control mechanisms of the body. Once they are understood, the etiologies of the disease states of hypoglycemia and resultant hyperactivity can be recognized. Finally, with all of this knowledge in place, the new therapies can be described.

Glucose is the main energy substance of the body and the blood is the means for transporting it to the various parts of the body. The blood glucose may be elevated by increasing its supply or blocking its removal. Conversely, blood glucose may be decreased by blocking its supply or enhancing its rate of removal from the blood.

There are two sources of blood glucose. Blood contains glucose, usually ingested in the form of starch or dissaccharids and converted to glucose by enzymes. The liver can also synthesize glucose from other food nutrients such as simple sugars or amino acids which are derived from protein digestion. Therefore, the blood level of glucose is a summation of the functions of its rate of entry into the blood and its rate of removal. The prior means of control of the blood level is summarized as follows:

| Prior Knowledge Limits in Regulation of Blood Glucose Levels | |
|---|---|
| Factors that Elevate Glucose | Factors that Lower Blood Glucose |
| 1. Ingested Food (i.e., starch, sugar) | 1. Fasting and Exercise |
| 2. Hepatic Glucose Production | 2. Hormone Stimulated Glucose removal from blood |
|   a. Glucose release from glycogen stimulated by glucagon, nor-epinephrine or epinephrine. |   a. Insulin stimulates muscle and fat cells to take up glucose. |
|   b. Glucose synthesized by glucagon stimulation from protein. | 3. Hormone mediated inhibition of hepatic glucose production. |
| |   a. Insulin alone inhibits the glucagon stimulated production of glucose by the liver - both synthesis and release. |

Insulin is a well-known polypeptide hormone that was discovered in 1922. Insulin is released from the beta cells of the pancreas in response to elevated blood glucose. Insulin has the known actions of (1) inhibiting the denovo synthesis and release of glucose from the liver and (2) stimulating the uptake of glucose by muscle and fat tissues. Therefore, insulin has the net effect of lowering blood glucose. This invention has its genesis in the recognition that although it is commonly known that the liver stores ingested glucose as glycogen, the hormonal control mechanism for this glucose storage of glycogen has been unknown.

It has been hypothesized that insulin must stimulate the hepatic deposition of glycogen. However, the addition of insulin alone to liver tissue bathed in glucose solutions does not result in glycogen storage as is seen when insulin is added to muscle tissue bathed in a glucose solution. Prior to the discovery upon which the present invention is based, experts in the actions of insulin, based upon many scientific studies, attribute it to be simply an inhibitor of hepatic glucose production.

SUMMARY OF THE INVENTION

The method of using known serotonin blocking agents to implement the discovery that both insulin and serotonin are required to cause the hepatic uptake of glucose, and that a disease which prevents the normal termination of serotonin production when digestion of food terminates production of glucose, will program the liver for uptake when it should begin glucose supply. Low glucose will cause the "fight and flight" syndrome which produces mental and physical disorders, including hyperkinetic behavior. This invention, therefore, will terminate the serotonin cofactor in timed relationship with termination of glucose supply to the portal vein of the liver.

This invention and discovery has resulted from observation and in vivo testing, in which it has been discovered that insulin alone is not responsible for liver uptake of glucose, but that a cofactor is essential. That cofactor is serotonin. Therefore, according to this invention and discovery, serotonin should be present when there is no peripheral need for glucose and should be absent when the liver is called upon to supply glucose for the peripheral needs.

The method of this invention, therefore, is to supply serotonin antagonist agents and/or agents to block production of serotonin in timed relationship to food ingestion, as symptoms dictate.

The medications of preference are cyproheptadine and methysergide.

DETAILED DESCRIPTION

Preferred Embodiment Method

Figure 1:
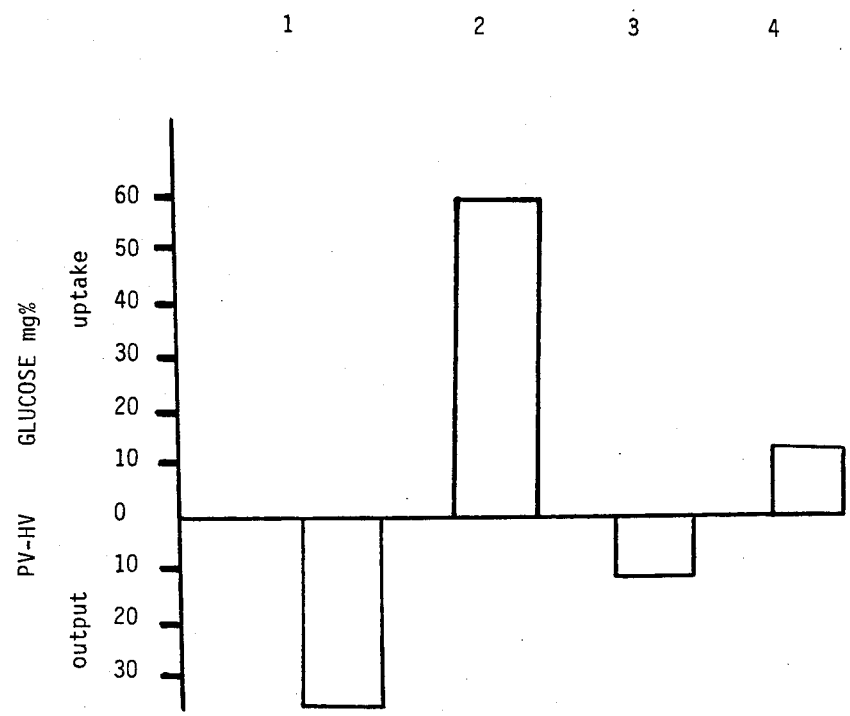
FIG. 1 is a chart which summarizes several clinical tests conducted in this study.

Long and careful study of the liver and its role in disorders and treatments of diseases of glucose metabolism has led to the discovery by this inventor that there is a glucose sensor mechanism in the portal circulatory system that is alerted when the glucose levels of portal blood exceed the glucose values elsewhere in the body.

Portal circulation is that circulatory system in which the portal vein and its branches collect blood from abdominal viscera and convey it to the sinusoids of the liver from which it then passes via the hepatic veins to the inferior vena cava (*Tabor's Cyclopedic Medical Dictionary*, F. A. David Company, 1982).

The discovery further embraces the new and novel concept that insulin alone is not the control that regulates production and storage of glycogen in the liver, and the controlled conversion of glycogen to glucose for release to the blood. Studies have led to the discovery by this inventor that there is a joint factor which cooperates with the insulin; that factor is serotonin(5-hydroxytryptamine or 5HT).

Serotonin is a hormone widely distributed throughout the warm-blooded animal body and is a necessary hormone for a number of bodily functions. For example, serotonin has the normal function of causing small blood vessels to constrict in the area of a hemorrhage. The smooth muscle of the alimentary tract is naturally stimulated by serotonin and thus participates in the normal control of intestinal motility. The heart is stimulated by serotonin to beat both more vigorously and rapidly. These actions of serotonin are well-known and have been recently reviewed (Goodman & Gilman's *The Pharmacologic Basis of Therapeutics*, 6th Edition, Macmillan Publishing Co., New York, 1980, pp. 633-639).

According to the research leading to this invention, it has also been hypothesized that serotonin is a hormone that is released into the portal circulation during the absorption of carbohydrate-containing food. The hypothetical relationship of serotonin to sugar intake in the liver has not been appreciated and, hence, medical literature lacks instruction of the etiology of disease such as hypoglycemia in the cooperation of insulin and serotonin in liver and blood sugar functions.

Hence, such research as directed by the hypothesis has led to an understanding of the etiology of hypoglycemia in particular and the serotonin relationship to liver functions in general.

This new hypothesis has led to the discovery that, upon ingesting food, the body senses a greater concentration of glucose in the portal circulation than in other blood circulatory systems. The only time the portal glucose level is higher than the peripheral level is when food is being absorbed after a meal. At that time, it has been found, serotonin is produced and carried with the glucose in the portal blood to the liver. Serotonin has been found to work in conjunction with insulin to cause the liver to convert the excess glucose absorbed from the meal to liver glycogen for regeneration as glucose by the body during period of fasting.

It has been established that in the absence of serotonin, the liver, even though supplied with an adequate amount of insulin, fails to properly convert the ingested glucose in the portal blood to glycogen and store it in the liver. The glucose is passed on from the liver to the rest of the body. The absence of serotonin in this case causes diabetes mellitus.

This inventor has also established that as long as serotonin is supplied to the liver in the presence of proper insulin levels the conversion of glucose to glycogen will not stop. If this occurs when food is not being absorbed, the liver takes up glucose instead of producing glucose, and the disease hypoglycemia occurs.

If the blood sugar falls to dangerously low levels, the body releases epinephrine and glucagon to counteract the serotonin and insulin effect, but only until the blood glucose is raised to usual fasting levels. At that time the epinephrine and glucagon release is stopped and the serotonin and insulin effect continues and hypoglycemia again occurs. The cycle of sympathetic release then repeats, followed again by the hypoglycemia, etc.

In study and experiments the relationship of the cyclic hypoglycemia/epinephrine syndrome to abnormalities characterized by hyperactivity became apparent. It has been discovered, according to this invention, that hypoglycemia untreated is a principle cause of hyperactivity. Thus, the cure for hyperkinetic conditions is first to stop liver uptake of glucose whenever there is no longer a supply of glucose in the portal vein.

The disease hypoglycemia has been noted in medical literature to be without known cause. Insulin excess can cause hypoglycemia, but this occurs only rarely. According to this invention, the common cause of hypoglycemia is the inappropriate release of portal serotonin when intestinal glucose absorption has ceased. Since insulin is nearly always present in the portal blood, its combined effect with the inappropriately released serotonin is to stop hepatic glucose production and start hepatic glucose storage. This situation leads to hypoglycemia since in the fasting state the liver is the body's only source of blood glucose. The epinephrine release then is triggered, and the abnormal cycle begins.

The body must avoid hypoglycemia and have adequate sources of glucose for energy. The brain, for example, must have an adequate and constant supply of glucose. A failure to have adequate glucose for the brain is as catastrophic as not having enough oxygen. A deprivation of glucose for only a few minutes can lead to irreversible organic brain damage.

When hypoglycemia occurs the body invokes an emergency hormone system, the adrenergic system, which temporarily stops the hepatic glucose uptake and switches the liver to producing glucose for the rest of the body. The adrenergic hormones that do this also cause the well-known "fight and flight" symptoms of agitation, sweating, and hyperactivity. In fact, the symptoms of hypoglycemia and hyperactivity are not really due to the low levels of blood glucose, per se, but due probably to these adrenergic hormones.

Adrenergic nerve stimulation (epinephrine and norepinephrine) and glucagon can convert the liver from glucose uptake even in the presence of serotonin. However, this adrenergic (sympathetic) nerve response stops after glucose values reach the normal fasting level. If the serotonin release is continuing, then the hepatic glucose uptake returns and another hypoglycemic episode occurs, to be followed by another sympathetic response, etc., not to be broken until food is eaten.

Thus, this invention has established that to control hyperactivity and hypoglycemia, the production of serotonin must be stopped or means supplied to block the effect of the serotonin after a sufficient amount of conversion and storage of glucose has been accomplished, and before the blood sugar level of the patient has fallen below acceptable levels.

It must be understood that in making this disclosure of the normal physiological control mechanisms of the body there is no clear understanding by the medical profession of all cause and effect leading to the symptoms of the disease known as hyperactivity. There is certainty, however, of the control by means of this invention.

Reactive or functional hypoglycemia is a disease classification which is an association between the well-known symptoms and an abnormally low blood glucose. This association between symptoms and the biochemical abnormality of low blood glucose is not easily demonstrated. In fact, clinical investigators have had great difficulty in proving beyond all of doubt that the symptoms are really due to the hypoglycemic state.

The real situation, physiologically, as has been established according to this invention:

1. Hypoglycemia occurs in response to an inappropriate release of portal serotonin.

2. The decrease in glucose level may be enough to trigger the compensatory sympathetic nervous system response, but not low enough to be considered "hypoglycemic" by the usual biochemical values. Thus, the cause and cure, heretofore, of hyperactivity has been elusive. Further, because all cases of hyperactivity are not related to hypoglycemia, the relationship prior to this invention has been elusive. In other words, any particular individual's norms may be narrower than the population norms. Biochemically this is a real problem because in a majority of cases there is no way to biochemically diagnose the disease. The fact that biochemically one cannot diagnose the problem of low blood sugar does not prevent the adequate treatment of "hypoglycemic and hyperactivity symptoms" according to the teaching of this invention with serotonin antagonist, i.e., cyproheptadine, methysergide, or other proven antagonist.

Therefore, this invention is successful for both situations: (1) hyperactivity symptoms correlated with low blood glucose values and (2) hyperactivity symptoms without corroborating laboratory data.

According to the hypothesis of this discovery, the symptoms of hyperactivity should occur after the lowest level of blood glucose and not simultaneous with it since the symptoms are probably due to adrenergic response and not hypoglycemia. This might explain the lack of correlation between symptoms and biochemical low blood glucose that troubles the present medical practitioner.

To prove the role serotonin plays in improper uptake, it is first necessary to establish the total roll serotonin plays. Hence, the immediately following experiments are to establish that without serotonin, little or no glucose is taken up and stored by the liver.

The necessity for the introduction of serotonin into the portal vein in order to cause the hepatic storage of glucose eaten in a meal has been proven in two different studies in a dog model which mimics the early stage of adult onset diabetes (Type II). In this model, adult onset diabetes, conventionally thought to be caused solely by lack of hepatic insulin, was induced in healthy mongrel dogs by selective denervation of the glands which secrete serotonin into the portal vein blood during a carbohydrate meal. These serotonin glands respond through the nervous system when glucose is being absorbed into the portal blood from the small intestine, and they normally cease producing serotonin when the meal has been absorbed.

In the first study a normal dog was anesthetized and catheters were surgically placed in the portal (the main blood supply to the liver) and hepatic veins (the main blood vessel leaving the liver) for the purpose of simultaneously measuring the glucose levels of the blood entering and exiting the liver. If the glucose level is higher in the portal than the hepatic vein, the liver is taking up and storing glucose. If, on the other hand, the hepatic vein glucose level is higher than the portal vein the liver is producing (releasing) glucose to supply the glucose needs of the rest of the body. The chart of FIG. 1 summarizes the several clinical tests conducted in this first study.

In the resting state of fasting (as opposed to eating), the liver should be producing glucose. Refer to the chart of FIG. 1. This output of glucose is seen in the first column, experimental period #1 called the "baseline" (hepatic values higher than portal). In period #2 glucose is infused into the portal vein (0.5 g glucose/kg body wt./hour) and the liver switches from output to glucose uptake. In period #3 the portal glucose infusion is maintained, but the nerve supply to the serotonin secreting cells is severed, stopping the release of serotonin and the animal switches back to glucose output. Finally, in period #4 serotonin is infused into the portal vein (30 ug/kg/min.) in sufficient quantity to mimic the normal secretion of serotonin, and the animal converts back to hepatic glucose uptake. Thus, the serotonin restored a normal physiological response to the glucose infusion.

This study teaches that the normal delivery of the 5HT in the portal vein to the liver can be surgically terminated. The deficiency of 5HT thus created produces the effect of continuous hepatic glucose output. Then, by direct delivery of 5HT to the liver by intraportal infusion and the resultant hepatic uptake, it is established that serotonin is, in fact, necessary along with insulin to cause hepatic glucose uptake.

Figure 2:
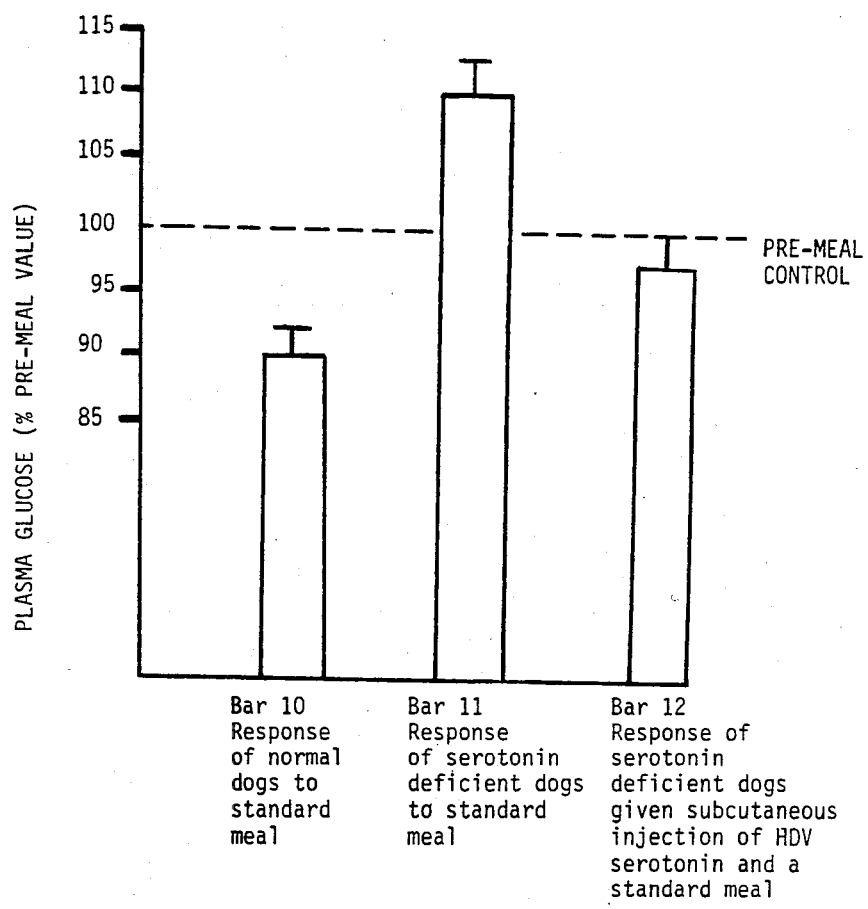
FIG. 2 is a graph of an average obtained from four dogs studied over several weeks using themselves as controls, followed by demonstration and this stabilization of this invention.

A second study used four healthy mongrel dogs to demonstrate this role of serotonin in glucose metabolism. The dogs were studied over several weeks using them as their own controls. The dogs were given a standard meal followed by taking peripheral venous blood samples at hourly intervals for four hours. The data are expressed as an average of the four dogs. This data is depicted in FIG. 2.

Bar 10 represents the normal small decrease in blood glucose levels that occurs following a meal. After the normal pattern of glucose levels in response to a meal was established, the dogs were anesthetized and the serotonin-secreting glands were denervated. The dogs were rested a week's time to permit healing. Then the dogs were again given a standard test meal, followed by hourly blood samples for glucose. Bar 11 represents the findings of the denervation caused the dogs to have hyperglycemic response to the meal, compared to the pre-denervation data (bar 10).

Several days later the dogs were injected subcutaneously with a small dose of serotonin (0.5 microgram serotonin/kg body wt) in the vesicle delivery system of the U.S. Pat. No. 4,603,044 issued July 29, 1986. This means of delivery was chosen because free serotonin is so avidly taken up by the peripheral tissues of the body that the free serotonin fails to reach the liver. Immediately following the injection of the HDV-serotonin the dogs were given the standard meal followed by hourly blood samples for glucose. Bar 12 clearly shows that the dogs' responses to the serotonin delivered to the hepatocytes and the meal were more like their normal predenervation response (bar 10) and statistically lower than the post denervation (no serotonin) response (bar 11).

The conclusion from these two studies was that serotonin is a hepatic neuromediator required for the normal response of hepatic glucose storage during a carbohydrate meal. The corollary to this conclusion is that serotonin in the portal blood during times of fasting, along with insulin which is nearly always present, would result in an inappropriate hepatic uptake of glucose and, therefore, hypoglycemia, since the blood's glucose comes only from the liver. That is to say that if the liver is storing glucose, it cannot simultaneously be supplying glucose. The tissues of the body are at the same time consuming glucose; therefore, hypoglycemia occurs. If, therefore, serotonin at the liver caused hypoglycemia, a serotonin antagonist at the liver should prevent hypoglycemia. It may be fairly stated that this invention resides as much, or more, in the discovery that the cause of hyperactivity is the disease hypoglycemia, as it does in the means to correct the malfunction.

Thus, an extremely important and novel new use has been discovered for an old and well-known chemical substance which functioned to block serotonin. Cyproheptadine has not heretofore been administered knowingly to patients to control the uptake of glucose by the liver.

Hence, a new treatment for hypoglycemia has been discovered using a serotonin blocking agent, administered in timed relationship to an empirically determined body function whereby glucose storage is terminated and liver supply of glucose to the body initiated. It has been established that blocking the production, storage, or function of serotonin by any blocking agent will produce the desired liver function control, but Cyproheptadine is a preferred substance because of its known low side reaction potential.

Functional hypoglycemia is due to a release of portal serotonin at a time when gastrointestinal absorption has been completed. The insulin which is correctly present in the portal blood at this time to normally inhibit hepatic glucose production, acts in concert with serotonin to stimulate hepatic glucose uptake. Since there is then no source of glucose for the body (food absorption has ceased and the liver is in uptake) the utilization of glucose by the body depletes the available surplus and produces hypoglycemia.

The body reacts to severe hypoglycemia with a large release of adrenergic mediators and glucagon. These agents stop the action of serotonin and convert the liver to producing and releasing glucose to supply the body's needs.

However, this defense system causes the well-known "fight and flight" response. Blood glucose goes up and down cyclically in response to serotonin, then adrenergics, then serotonin, etc. The control is poor and the patient is in obvious distress, often manifested by hyperactivity.

The preferred means of therapy for hypoglycemia of this type is a specific blockage of the serotinergic receptor of the hepatocyte by serotonin antagonists. Two examples of oral ingested blockers are methysergide and cyproheptadine. Of these two examples, methysergide is less preferred because of greater possibility of undesirable side effects. Both agents block serotonin's effects on hepatic glucose uptake. The selected agent is administered thirty to sixty minutes prior to the onset of symptoms (these are readily predicted by the patient). Full relief is thus obtained.

Cyproheptadine is a serotonin antagonist and is the preferred material. Other agents in this class are methysergide (a derivative of lysergic acid); indole compounds such as gramine, hormine and tryptamine; arylguandes and biguanides; histamin $H_1$ blockers of the ethylene diamine type; phenothiazines such as phenoxybenzamines.

Less preferred but workable means to treat hypoglycemia include drugs which generally lower body levels of serotonin. These include the following:
1. Drugs which inhibit serotonin synthesis:
   a. para chlorophenylalanine
   b. para chloroamphetamine
   c. amino acid derivatives of 6-flourotryptophan
2. Drugs which inhibit serotonin membrane uptake:
   a. tertiary amines such as chloroimipramin, imipramine and amitriptyline
   b. fluoxetine
3. Drugs which inhibit serotonin storage:
   a. reserpine
   b. tetrabenazine
   c. fenfluramine While serotonin antagonists such as cyproheptadine are the preferred class for treating and preventing hypoglycemia, it must be recognized that they block all serotonin actions all over the body and thus may induce many side effects such as sedation, sleepiness, dizziness, disturbed coordination, confusion, restlessness, rashes, blurred vision, hypotension, anemias, anorexia, to name a few. These nonspecific effects of this class of materials can be overcome by utilizing a bipolar lipid membrane delivery system specific for the hepatocytes to deliver these materials only to the serotonin receptors responsible for the glucose effects in the liver. Thus, all other serotonin mechanisms in the body remain unaffected. This hepatocyte delivery of serotonin antagonists is the ultimate form of treatment for hypoglycemia and hyperkinetic behavior. The hepatocyte delivery vesicle is taught in U.S. patent application Ser. No. 456,270 filed Jan. 6, 1983, specifically incorporated by reference and now abandoned.

What is claimed is:

1. The method of averting hyperactive behavior caused by excess serotonin being present in the portal venous blood after the level of glucose present in the portal venous blood has dropped due to the substantial completion of absorption of carbohydrate-containing food from the gastrointestinal tract followed by activation of the adrenergic nervous system, which in turn produces a low blood glucose again, comprising administering to said warm blooded animal having hyperactive behavior caused by excess serotonin, an effective dose of serotonin antagonist selected from the group consisting of cyproheptadine, methylsergide and 6-flurotryptophan.

2. A method for averting alternate excess blood sugar and low blood sugar, comprising administering orally to a warm blooded animal exhibiting a history of hyperactivity behavior, a serotonin inhibiting amount of serotonin antagonist selected from the group consisting of cyproheptadine, methylsergide, and an amino acid derivative of 6-fluorotryptophan after a meal and the level of glucose present in the portal venous blood has dropped due to substantial completion of absorption of food, thereby inhibiting glucose uptake by the liver and providing glucose for the peripheral blood supply, whereby the adrenergic nervous system response is averted.

3. The method of claim 1 wherein the serotonin antagonist is administered to the host within 2–4 hours after ingestion of food.

4. The method of claim 1 wherein the administered therapeutic dose is a drug which will inhibit serotonin membrane uptake selected from class consisting of: cyproheptadine, methysergide and 6-fluorotryptophan.

5. The method of claim 1 wherein the administered therapeutic dose is a drug which will inhibit serotonin storage, selected from the class consisting of: cyproheptadine, methysergide and 6-fluorotryptophan.

* * * * *